United States Patent [19]
Brunelle et al.

[11] Patent Number: 5,821,322
[45] Date of Patent: Oct. 13, 1998

[54] DIAMINOALKYL QUATERNARY AMMONIUM SALTS AND METHOD FOR THEIR PREPARATION AND USE

[75] Inventors: Daniel Joseph Brunelle, Burnt Hills; Peter David Phelps, Schenectady; Eugene Pauling Boden, Scotia, all of N.Y.; Mark Erik Nelson, Mt. Vernon, Ind.; Larry Ivis Flowers; Paul Dean Sybert, both of Evansville, Ind.; Erik Hendrick Adriaan Capelle, Oud Vossemeer, Netherlands

[73] Assignee: General Electric Company, Schenectady, N.Y.

[21] Appl. No.: 851,260

[22] Filed: May 5, 1997

[51] Int. Cl.$^6$ ........................................ C08G 64/00
[52] U.S. Cl. ........................ 528/199; 502/150; 502/164
[58] Field of Search ............................. 528/199; 502/150, 502/164

[56] References Cited

U.S. PATENT DOCUMENTS 5,391,692  2/1995  Boden et al. .......................... 528/199
5,510,449  4/1996  Flowers et al. ......................... 528/199
5,519,105  5/1996  Boden et al. .......................... 528/199

*Primary Examiner*—Terressa Mosley
*Attorney, Agent, or Firm*—Noreen C. Johnson; Douglas E. Stoner

[57] ABSTRACT

Diaminoalkyl quaternary ammonium salts are prepared by the reaction of alkyl halides with tertiary diamines having $C_{2-20}$ primary alkyl radicals attached to nitrogen and an alkyl radical between the two nitrogen atoms in which at least three carbon atoms separate said nitrogen atoms. Said salts are preferably substantially free from corresponding diamines. They are useful as catalysts for interfacial polycarbonate preparation by the reaction of phosgene with at least one dihydroxyaromatic compound. Polycarbonate preparation using such catalysts is economical in phosgene consumption, is accompanied by a rapid conversion of chloroformate groups to desirable species and affords a product with a very low proportion of unreacted dihydroxyaromatic compound.

20 Claims, No Drawings

DIAMINOALKYL QUATERNARY AMMONIUM SALTS AND METHOD FOR THEIR PREPARATION AND USE

BACKGROUND OF THE INVENTION

This invention relates to the interfacial preparation of polycarbonates, and more particularly to the improvement of catalyst species used therein.

The so-called "interfacial method" for polycarbonate preparation involves the reaction of at least one dihydroxyaromatic compound with phosgene in a basic aqueous-organic medium, in the presence of a suitable catalyst. The resulting polycarbonate migrates to the organic phase and may be recovered therefrom.

It has long been known that tertiary amines, especially trialkylamines such as triethylamine, can be employed as catalysts for the interfacial preparation of polycarbonates. However, the use of tertiary amines as catalysts requires the employment of a considerable excess of phosgene, typically about 10–15% over stoichiometric, since phosgene hydrolysis is a principal side reaction.

In recent years, as illustrated, for example, in U.S. Pat. No. 5,391,692, it has been discovered that phase transfer catalysts such as quaternary ammonium halides and quaternary phosphonium halides can replace tertiary amines as catalysts for interfacial polycarbonate preparation, thereby improving utilization of phosgene. However, the use of such catalysts also suppresses the conversion of chloroformate-terminated intermediate polymers to useful species, most often endcapped or hydroxy-terminated polycarbonates. Since chloroformate-terminated species may be produced in significant proportions and since their presence in the polycarbonate product is undesirable, the use of phase transfer catalysts with its concomitant improvement in phosgene usage has not been widely employed on a commercial scale. Chloroformate formation and slowness to convert to less detrimental species, and long polymerization times coupled with mandatory further additions of phosgene to produce a polymer of the desired molecular weight, are hereinafter collectively designated "end point problems".

Still more recently, it has been discovered and disclosed in U.S. Pat. Nos. 5,519,105 and 5,510,449 that the employment of a combination of phase transfer catalyst and tertiary amine can result in efficient phosgene usage and improved conversion of chloroformate-terminated polymers to useful products. The use of two catalytic species in combination, however, has its own disadvantages including the necessity of employing two separate schemes for recovering catalyst.

It has also been found that the employment of tertiary amines in the interfacial preparation of polycarbonates can result in relatively high (e.g., 6 ppm by weight or greater) proportions of residual monomeric dihydroxyaromatic compound in the polycarbonate product. While such a proportion may be insignificant in many areas of use, it is undesirable when employment of the polycarbonate in contact with food or beverages is intended. An example of such use is in the fabrication of water bottles.

Finally, it is important from a commercialization standpoint that procedures for handling and recovering catalyst materials for recycle be as similar as those employed with the conventional tertiary amines. The conventional procedures include separation of the aqueous and organic phases, during which it is preferred that the major proportion of catalyst be in the organic phase; aqueous acidic wash of the organic phase, during which as much catalyst as possible should transfer to the wash liquid; and subsequent recovery of the catalyst from the wash liquid for recycle.

It continues to be of interest, therefore, to develop new catalytic species for interfacial polycarbonate preparation which have the above-described properties.

SUMMARY OF THE INVENTION

The present invention is based on the discovery of a new class of organic compounds which combine in a single molecule the tertiary amine and quaternary ammonium salt functionalities. These compounds may be employed as catalysts for interfacial polycarbonate preparation, and when so employed they combine the benefits of efficient phosgene usage, rapid conversion of chloroformate groups and very low proportions of dihydroxyaromatic compound in the polycarbonate product.

One aspect of the invention is diaminoalkyl quaternary ammonium salts (hereinafter sometimes simply designated "amino salts" for brevity) having the formula

wherein:
each of $R^1$, $R^2$, $R^4$, $R^5$ and $R^6$ is a $C_{1-20}$ primary alkyl radical, or at least one of the combinations of $R^1$ and $R^2$ with the nitrogen atom connecting them, and $R^4$ and $R^5$ with the nitrogen atom connecting them, form a pyrrolidine or piperidine ring;

$R^3$ is a $C_{2-20}$ alkylene radical wherein at least 2 carbon atoms separate the two nitrogen atoms; and Z is one equivalent of an anion.

Another aspect is a method for preparing such salts substantially free from corresponding diamines which comprises contacting a tertiary aliphatic or alicyclic diamine having at least 2 carbon atoms separating the two nitrogen atoms with a $C_{1-20}$ alkyl halide at a temperature in the range of about 20°–150° C., the molar ratio of said diamine to said halide being at least 1:1, and subsequently removing unreacted diamine by dissolving the amino salt in a basic aqueous medium and extracting said medium with an organic liquid of low polarity.

Still another aspect is a method for preparing a polycarbonate which comprises contacting at least one dihydroxyaromatic compound with phosgene in a basic aqueous-organic system, in the presence of a catalytically effective proportion of an amino salt as described hereinabove.

DETAILED DESCRIPTION; PREFERRED EMBODIMENTS

The $R^1$, $R^2$ and $R^{4-6}$ radicals in the amino salts of this invention are $C_{1-20}$ primary alkyl radicals. Methyl radicals are, however, not preferred since the compounds containing them are similar to trialkylamines in causing significant phosgene hydrolysis. Thus, the preferred $R^1$, $R^2$ and $R^{4-6}$ radicals contain 2–20 and especially 2–8 carbon atoms.

It is also within the scope of the invention for at least one of $R^{1-2}$ and $R^{4-5}$ to form with the associated nitrogen atom a heterocyclic ring; i.e., pyrrolidine or piperidine which may be unsubstituted or substituted. Such compounds, while not "diaminoalkyl quaternary ammonium salts" as strictly defined, are equivalent thereto. However, such compounds are generally not preferred since they tend to exhibit increased phosgene hydrolysis when employed in polycarbonate preparation.

The $R^3$ radical is an alkylene radical containing 2–20 carbon atoms, at least 2 of which are in a chain separating the two nitrogen atoms. Since compounds in which $R^3$ is the ethylene radical exhibit significant end point problems when employed as catalysts, $R^3$ preferably has at least 3 and most preferably 3–10 carbon atoms and the nitrogen atoms are separated by a chain of at least 5 of said carbon atoms. The Z radical is one equivalent of an anion, usually a monovalent anion and most often hydroxide, chloride or bromide.

Said salts may be prepared by the reaction of a corresponding diamine, typically one of the formula

(II)

wherein $R^{1-5}$ are as previously defined, with a $C_{1-20}$ alkyl halide, most often having the formula $R^6Z$ in which Z is chloride or bromide as previously defined. The reaction typically takes place at a temperature in the range of about 20°–150° C. and most often in an organic solvent. Illustrative solvents include aliphatic nitriles such as acetonitrile, halogenated aliphatic hydrocarbons such as methylene chloride and chloroform, aromatic hydrocarbons such as toluene and xylene and dipolar aprotic solvents such as dimethylformamide, dimethyl sulfoxide and N-methylpyrrolidone. An inert atmosphere, such as nitrogen or argon, is often preferred.

To suppress the formation of bis-quaternary ammonium salts, it is preferred that the molar ratio of diamine to alkyl halide be at least 1:1. Ratios of at least 2:1 are preferred, since sizable proportions of bis-quaternary ammonium salt may be produced as by-products at lower molar ratios.

The product of this reaction will ordinarily be a mixture of unreacted diamine, bis-quaternary ammonium salt and the amino salt of the invention. If conversion to the hydroxide is desired, it may be achieved by reaction with a suitable alkali metal hydroxide.

If the product is employed in crude form for polycarbonate formation, the presence of a substantial proportion of diamine may cause an increase in phosgene usage. On the other hand, the presence of small proportions of bis-quaternary ammonium salt may not be particularly disadvantageous since it may also act as a phosgenation catalyst and the amine group concentration, from the amino salt, is high enough to afford rapid reaction of chloroformate groups.

It is strongly preferred, therefore, to isolate the amino salt substantially free from unreacted diamine. By "substantially free from" is meant that the purified amino salt has a diamine content of no more than 1.0% and preferably no more than 0.1% by weight. This may be achieved by dissolving the product in a basic aqueous medium, typically aqueous alkali metal hydroxide and preferably sodium hydroxide having a concentration in the range of about 0.1–0.5M, thereby maintaining all unreacted diamine in the free form, and extracting said basic aqueous medium with an organic liquid of low polarity, which dissolves said diamine and which can then be readily separated from the aqueous medium. Illustrative organic liquids which may be used for this purpose are aliphatic hydrocarbons such as hexane, octane, decane and petroleum ether and aromatic hydrocarbons such as toluene and xylene.

Following diamine removal, the amino salt may be recovered by conventional techniques. Such techniques may involve operations such as salting out of aqueous solution, extraction into an organic solvent and stripping.

The preparation of the amino salts of this invention is illustrated by the following examples.

EXAMPLE 1

A mixture of one equivalent of 1,3-bis(n-pentylamino) propane, one equivalent of ethyl bromide and 50 ml of methylene chloride was allowed to stand until a precipitate was formed, and was then heated under reflux for 2 hours. The precipitate was removed by filtration. Upon carbon-13 nuclear magnetic resonance spectroscopy of the filtrate and the precipitate, it was found that the precipitate was the bis-quaternary ammonium salt and the filtrate contained unreacted diamine in combination with the desired 3-(di-n-pentylamino)propyl-di-n-pentylethylammonium bromide.

EXAMPLES 2–5

The procedure of Example 1 was repeated, employing various diamines and alkyl bromides as shown in Table I. The products obtained were similar to that obtained in Example 1.

TABLE I

| Example | $R^{1-2, 4-5}$ | $R^3$ | $R^6$ |
|---|---|---|---|
| 2 | n-Pentyl | Trimethylene | n-Pentyl |
| 3 | n-Propyl | Hexamethylene | n-Propyl |
| 4 | n-Pentyl | Nonamethylene | Ethyl |
| 5 | n-Pentyl | Nonamethylene | n-Pentyl |

EXAMPLE 6

A mixture of 20 mmol of 1,6-bis(diethylamino)hexane, 10 mmol of n-hexyl bromide and sufficient acetonitrile to effect dissolution was heated under reflux in a nitrogen atmosphere for 24 hours, whereupon it was shown by proton nuclear magnetic resonance spectroscopy that all the n-hexyl bromide had reacted. The mixture was diluted with water and made basic by the addition of 10 ml of 2M aqueous sodium hydroxide solution.

The resulting aqueous phase was washed 3 times with toluene to remove unreacted diamine, and the resulting aqueous solution was found to comprise 65% of the desired 6-(diethylamino)hexyldiethyl-n-hexylammonium bromide (65% yield based on n-hexyl bromide) and 35% of the corresponding bis-quaternary ammonium salt. A major proportion of the latter was precipitated by addition of ethyl acetate, after which the filtrate comprised 95% amino salt and 5% bis-quaternary ammonium salt.

Similar results were obtained when the reaction was carried out in toluene as solvent.

EXAMPLE 7

The procedure of Example 6 was repeated, employing diamine and n-hexyl bromide in a 4:1 molar ratio. The yield of the amino salt was 85%.

EXAMPLE 8

The procedure of Example 6 was repeated, employing dimethyl sulfoxide as a solvent. The yield of the amino salt was 80%.

EXAMPLES 9–18

The procedure of Example 6 was repeated with the use of various alkylenediamines and alkyl bromides as shown in Table II.

TABLE II

| Example | R$^{1-2, 4-5}$ | R$^3$ | R$^6$ |
| --- | --- | --- | --- |
| 9 | Methyl | Ethylene | n-Hexyl |
| 10 | Methyl | Ethylene | n-Octyl |
| 11 | Ethyl | Ethylene | n-Hexyl |
| 12 | Ethyl | Ethylene | n-Octyl |
| 13 | Ethyl | Hexamethylene | n-Octyl |
| 14 | Ethyl | Octamethylene | n-Hexyl |
| 15 | Ethyl | Octamethylene | n-Octyl |
| 16 | Piperidinyl* | Hexamethylene | n-Hexyl |
| 17 | Piperidinyl* | Hexamethylene | n-Octyl |
| 18 | R$^{1,3}$-n-Octyl R$^{2,4}$-Ethyl | Hexamethylene | n-Hexyl |

*With N.

The amino salts of this invention are, as previously stated, useful as catalysts for interfacial polycarbonate preparation. The polycarbonate-forming reaction takes place in a mixture comprising at least one dihydroxyaromatic compound, phosgene, an aqueous alkaline solution, a catalyst and a water-immiscible organic solvent.

It is also contemplated to include in the reaction mixture at least one monohydroxyaromatic compound as a chain termination agent. Suitable compounds of this type include phenol and p-cumylphenol. Also present may be an aromatic dicarboxylic acid or functional derivative thereof, such as a dialkyl ester, whereupon the product is a copolyestercarbonate.

Suitable dihydroxyaromatic compounds include those having the formula

$$HO-A^1-OH, \qquad \text{(III)}$$

wherein $A^1$ is a divalent aromatic hydrocarbon radical. Suitable $A^1$ radicals include m-phenylene, p-phenylene, 4,4'-biphenylene, 4,4'-bi(3,5-dimethyl)phenylene, 2,2-bis(4-phenylene)propane and similar radicals such as those which correspond to the dihydroxy-substituted aromatic hydrocarbons disclosed by name or formula (generic or specific) in U.S. Pat. No. 4,217,438.

The $A^1$ radical preferably has the formula

$$-A^2-Y-A^3-, \qquad \text{(IV)}$$

wherein each of $A^2$ and $A^3$ is a monocyclic divalent aromatic hydrocarbon radical and Y is a bridging hydrocarbon radical in which one or two atoms separate $A^2$ from $A^3$. The free valence bonds in formula III are usually in the meta or para positions of $A^2$ and $A^3$ in relation to Y. Compounds in which $A^1$ has formula IV are bisphenols, and for the sake of brevity the term "bisphenol" is sometimes used herein to designate the dihydroxy-substituted aromatic hydrocarbons; it should be understood, however, that non-bisphenol compounds of this type may also be employed as appropriate.

In formula III, the $A^2$ and $A^3$ values may be unsubstituted phenylene or hydrocarbon-substituted derivatives thereof, illustrative substituents (one or more) being alkyl and alkenyl. Unsubstituted phenylene radicals are preferred. Both $A^2$ and $A^3$ are preferably p-phenylene, although both may be o- or m-phenylene or one o- or m-phenylene and the other p-phenylene.

The bridging radical, Y, is one in which one or two atoms, preferably one, separate $A^2$ from $A^3$. Illustrative radicals of this type are methylene, cyclohexylmethylene, 2-[2.2.1]-bicycloheptylmethylene, ethylene, isopropylidene, neopentylidene, cyclohexylidene, cyclopentadecylidene, cyclododecylidene and adamantylidene; gem-alkylene (alkylidene) radicals are preferred. Also included, however, are unsaturated radicals. For reasons of availability and particular suitability for the purposes of this invention, the preferred bisphenol is 2,2-bis(4-hydroxyphenyl)propane ("bisphenol A"), in which Y is isopropylidene and $A^2$ and $A^3$ are each p-phenylene.

The water-immiscible organic solvents which may be used in the interfacial polymerization reaction are conventional for such types of reactions. Methylene chloride is often preferred. The amount of catalyst present is an amount effective to promote interfacial condensation and polycarbonate formation, which is generally in the range of about 0.1–5.0 mole percent based on dihydroxyaromatic compound.

As previously mentioned, for the purpose of polycarbonate preparation the preferred catalysts are the compounds of formula I in which each of $R^1$, $R^2$, $R^4$ and $R^5$ contains at least 2 carbon atoms and $R^3$ has at least 3 carbon atoms separating the nitrogen atoms. The use of such compounds is particularly advantageous from the standpoints of phosgene usage and avoidance of end point problems.

The interfacial polymerization reaction is ordinarily carried out at a temperature in the range of about 10°–50° C. and preferably at ambient temperature. Phosgene is passed into the mixture at a suitable rate to effect polymerization, which rate may be determined by simple experimentation.

When the reaction with phosgene is complete, it may be necessary to continue to agitate the reaction mixture until chloroformate groups are converted. Following polycarbonate formation, the organic and aqueous phases may be separated and the polycarbonate isolated from the organic phase by anti-solvent precipitation or the like. Prior to polycarbonate isolation, however, it may be desirable to isolate the amino salt for recycle.

As between the organic and basic aqueous phases of the interfacial reaction mixture, the amino salt prefers to remain in the organic phase. This is confirmed by the partition coefficient $K_D$ of the salt (which for this purpose is considered to include its conversion product in basic medium, the corresponding amino hydroxide) between the two phases, which is defined as the concentration thereof in the aqueous phase divided by its concentration in the organic phase. The value of $K_D$ as between these two phases is uniformly less than 1.

Thus, a major proportion of the amino salt may be recovered for recycle by removal from the organic phase. One convenient way of doing this is by washing with dilute aqueous acid, typically having a concentration in the range of about 0.5–2.0M to convert the amino salt into its acidified form (i.e., the form in which the free amino group is protonated) which preferentially migrates to the aqueous acidic phase. The $K_D$ values as between the aqueous acidic wash liquid and the organic phase are very high, typically at least about 60. Thus, the vastly major proportion of the amino salt enters the wash liquid in its protonated form and may be regenerated and isolated by treatment with aqueous base.

Any remainder of the amino salt in the basic aqueous phase of the interfacial reaction mixture can be removed prior to recovery, if desired, of other values therefrom. A typical method of removal is by adsorption on a non-ionic polystyrene resin as disclosed, for example, in copending, commonly owned application Ser. No. 08/641,971.

In addition to minimizing phosgene hydrolysis and efficiently disposing of free chloroformate groups, the amino salts of this invention produce polycarbonates having very low proportions of unreacted monomer, frequently too low to be detectable. Thus, they are particularly useful for the production of polymers to be employed in contact with foods and beverages.

The interfacial preparation of polycarbonates by the method of this invention is illustrated by the following examples.

EXAMPLES 19–23

Three 500-ml, 5-necked Morton flasks, each fitted with a mechanical stirrer, phosgene dip tube, caustic addition port, pH electrode and chilled brine condenser vented to a basic methanol scrubber, were each charged with 38 g (167 mmol) of bisphenol A, 1.42 g (6.7 mmol) of p-cumylphenol, 200 ml of methylene chloride and 600 ml of water. Various amino salts of the invention were introduced as catalysts and phosgene was passed into each reaction mixture, with pH control in the range of 10.5–11.5.

Near the termination of the reaction, phosgene detection paper was used to determine the presence or absence of chloroformates and the time required to effect complete reaction thereof. The amount of phosgene required was determined from the amount of sodium hydroxide added to the reaction mixture, and the weight average molecular weight of the polycarbonate produced was determined by gel permeation chromatography relative to polystyrene.

The results are given in Table III, in comparison with two controls employing prior art catalysts, as follows:
Control 1—triethylamine,
Control 2—1,6-bis(octylpiperidinium)hexane dibromide.

TABLE III

| | Catalyst | | Chloroformate | Excess | |
|---|---|---|---|---|---|
| Example | Identity | Mole % | reaction time, min. | phosgene req., mole % | Product Mw |
| 19 | Ex. 6 | 0.6 | 2.5 | 8 | 41,700 |
| 20 | Ex. 16 | 0.3 | 3 | 9 | 40,900[1] |
| 21 | Ex. 17 | 0.3 | 4 | 8 | 40,100[1] |
| 22 | Ex. 12 | 0.3 | 3 | 5 | 41,000[1] |
| 23 | Ex. 11 | 1.0 | 150 | 4 | 41,200 |
| 24 | Ex 9 | 0.5 | — | 58 | 40,700 |
| Control 1 | Listed above | 1.0 | — | 18 | 42,900 |
| Control 2 | Listed above | 0.15 | 20 | 21 | 38,000 |

[1]Including phosgene added after thickening of the reaction mixture, probably due to mass transfer effects.

It will be apparent from Table III that the compounds of this invention offer significant advantages in minimizing phosgene usage and end point problems. The methyl-substituted amino salt (Example 24) is effective as a catalyst but requires usage of a considerable excess of phosgene. High phosgene consumption is also noted for reactions employing as catalysts triethylamine (Control 1) and a bis-quaternary ammonium salt (Control 2).

Residual monomeric bisphenol A in the product of Example 19 was separated by precipitating the polycarbonate from the acid-washed organic phase by pouring into hexane, filtering, drying, dissolving in chloroform and precipitating into acetonitrile, whereupon said bisphenol A remained in solution. Said level was too low to be detectable. By contrast, Control 1 had a bisphenol A level of 6.2 ppm.

EXAMPLE 24

The aqueous and organic phases in a reaction mixture corresponding to that of Example 5 were separated and analyzed for amino salt content. It was found that the distribution coefficient, $K_D$, was 0.22. Thus, a very high proportion of the amino salt was retained in the organic phase.

What is claimed is:

1. A diaminoalkyl quaternary ammonium salt having the formula

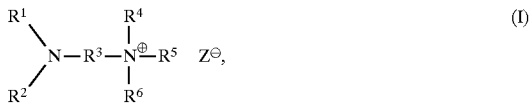

wherein:
each of $R^1$, $R^2$, $R^4$, $R^5$ and $R^6$ is a $C_{1-20}$ primary alkyl radical, or at least one of the combinations of $R^1$ and $R^2$ with the nitrogen atom connecting them, and $R^4$ and $R^5$ with the nitrogen atom connecting them, form a pyrrolidine or piperidine ring;
$R^3$ is a $C_{2-20}$ alkylene radical wherein at least 2 carbon atoms separate the two nitrogen atoms; and
Z is one equivalent of an anion.

2. A salt according to claim 1 wherein each of $R^1$, $R^2$, $R^4$, $R^5$ and $R^6$ is a $C_{2-20}$ primary alkyl radical and $R^3$ is a $C_{3-20}$ alkylene radical.

3. A salt according to claim 2 which is substantially free from unreacted diamine.

4. A salt according to claim 2 wherein Z is hydroxide, bromide or chloride.

5. A salt according to claim 4 wherein each of $R^1$, $R^2$, $R^4$, $R^5$ and $R^6$ is a $C_{2-8}$ primary alkyl radical.

6. A salt according to claim 4 wherein $R^3$ is a $C_{3-10}$ alkylene radical wherein at least 5 carbon atoms separate the two nitrogen atoms.

7. A salt according to claim 6 wherein each of $R^1$, $R^2$, $R^4$ and $R^5$ is ethyl, $R^6$ is n-hexyl or n-octyl and $R^3$ is hexamethylene.

8. A method for preparing a diaminoalkyl quaternary ammonium salt substantially free from corresponding diamines which comprises contacting a tertiary aliphatic or alicyclic diamine having at least 3 carbon atoms separating the two nitrogen atoms with a $C_{2-20}$ alkyl halide at a temperature in the range of about 20°–150° C., the molar ratio of said diamine to said halide being at least 1:1, and subsequently removing unreacted diamine by dissolving the amino salt in a basic aqueous medium and extracting said medium with an organic liquid of low polarity.

9. A method according to claim 8 wherein the molar ratio of said diamine to said halide is at least 2:1.

10. A method according to claim 9 wherein the diamine has the formula

and the halide has the formula $R^6Z$, wherein:
each of $R^1$, $R^2$, $R^4$ and $R^5$ is a $C_{1-20}$ primary alkyl radical, or at least one of the combinations of $R^1$ and $R^2$ with the nitrogen atom connecting them, and $R^4$ and $R^5$ with the nitrogen atom connecting them, form a pyrrolidine or piperidine ring; and
$R^3$ is a $C_{2-20}$ alkylene radical wherein at least 2 carbon atoms separate the two nitrogen atoms; and
Z is chloride or bromide.

11. A method according to claim 10 wherein each of $R^1$, $R^2$, $R^4$, $R^5$ and $R^6$ is a $C_{2-20}$ primary alkyl radical and $R^3$ is a $C_{3-20}$ alkylene radical.

12. A method according to claim 11 wherein the organic liquid is an aliphatic or aromatic hydrocarbon.

13. A method according to claim 12 wherein the organic liquid is toluene or petroleum ether.

14. A method for preparing a polycarbonate which comprises contacting at least one dihydroxyaromatic compound with phosgene in a basic aqueous-organic system, in the presence of a catalytically effective proportion of a diaminoalkyl quaternary ammonium salt having the formula

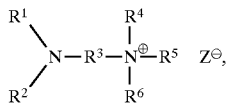  (I)

wherein:
each of $R^1$, $R^2$, $R^4$, $R^5$ and $R^6$ is a $C_{1-20}$ primary alkyl radical, or at least one of the combinations of $R^1$ and $R^2$ with the nitrogen atom connecting them, and $R^4$ and $R^5$ with the nitrogen atom connecting them, form a pyrrolidine or piperidine ring;

$R^3$ is a $C_{2-20}$ alkylene radical wherein at least 2 carbon atoms separate the two nitrogen atoms; and Z is one equivalent of an anion.

15. A method according to claim 14 wherein each of $R^1$, $R^2$, $R^4$, $R^5$ and $R^6$ is a $C_{2-20}$ primary alkyl radical and $R^3$ is a $C_{3-20}$ alkylene radical.

16. A method according to claim 14 wherein the polycarbonate is a bisphenol A polycarbonate.

17. A method according to claim 16 wherein the aqueous-organic system includes a water-immiscible organic solvent.

18. A method according to claim 17 wherein the organic solvent is methylene chloride.

19. A method according to claim 15 wherein the amino salt is present in the range of about 0.1–5.0 mole percent based on dihydroxyaromatic compound.

20. A method according to claim 15 wherein each of $R^1$, $R^2$, $R^4$ and $R^5$ is ethyl, $R^6$ is n-hexyl or n-octyl, $R^3$ is hexamethylene, Z is bromide or chloride and said aminoalkyl quaternary ammonium salt is substantially free from unreacted diamine.

* * * * *